United States Patent [19]

Szantay et al.

[11] 4,210,650

[45] Jul. 1, 1980

[54] ANTIPHLOGISTIC METHOD OF TREATMENT

[75] Inventors: Csaba Szántay; Lajos Szabó; László Töke; István Toth; Sándor Virág; Erzsébet Kanyó; Agoston Dávid, all of Budapest, Hungary

[73] Assignee: Chinoin Gyogyszer es Vegyeszeti Termekek Gyara RT., Budapest, Hungary

[21] Appl. No.: 13,271

[22] Filed: Feb. 21, 1979

Related U.S. Application Data

[63] Continuation-in-part of Ser. No. 744,608, Nov. 24, 1976, which is a continuation-in-part of Ser. No. 624,470, Oct. 21, 1975, Pat. No. 4,102,886.

[30] Foreign Application Priority Data

Oct. 23, 1974 [HU] Hungary ............................. C 1514
Sep. 11, 1975 [HU] Hungary ............................. C 1603

[51] Int. Cl.$^2$ ............................................. A61K 31/47
[52] U.S. Cl. .................................... 424/258; 546/65
[58] Field of Search ........................................ 424/258

*Primary Examiner*—Stanley J. Friedman
*Attorney, Agent, or Firm*—Karl F. Ross

[57] ABSTRACT

2-oxo-3-($\beta$-cyanoethyl)-9,10-methylenedioxy-1,2,3,4,6,7-hexahydro-11bH-benzo(a)quinolizidine (SC-118) especially and the corresponding 9,10-diethoxy compound are superior antiphlogistics which are used in effective amounts in antiphlogistic therapy.

3 Claims, No Drawings

ANTIPHLOGISTIC METHOD OF TREATMENT

CROSS-REFERENCE TO RELATED APPLICATIONS

This application is a continuation-in-part of copending application Ser. No. 744,608 filed Nov. 24, 1976 as a continuation-in-part of Ser. No. 624,470 filed Oct. 21, 1975 (now U.S. Pat. No. 4,102,886 of July 25, 1978). This application also relates to copending application Ser. No. 808,983 filed June 22, 1977 as a division of Ser.No. 744,608, now abandoned.

FIELD OF THE INVENTION

This invention relates to an improved antiphlogistic method of treatment.

DESCRIPTION OF THE INVENTION

According to the present invention benzo(a)-quinolizidine derivatives of the formula (II)

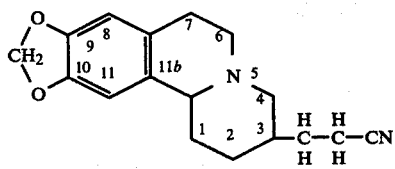

i.e. 2-oxo-3-($\beta$-cyanoethyl)-9,10-methylenedioxy-1,2,3,4,6,7-hexahydro-11bH-benzo(a)quinolizidine (SC-118) and

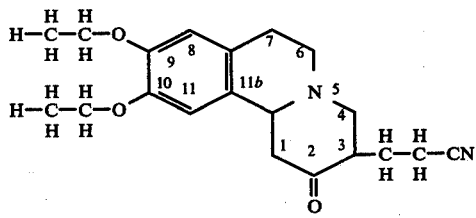

i.e. 2-oxo-3-($\beta$-cyanoethyl)-9,10-diethoxy-1,2,3,4,6,7-hexahydro-11bH-benzo(a)quinolizidine (SCT-3) and salts thereof having an antiinflammatory therapeutic effect, are used in antiphlogistic treatments.

In Hungarian Pat. Nos. 153,695 and 155,959 compounds of the formula (I) (below) are disclosed, wherein $R^1$ and $R^2$ are hydrogen, $R^7$ is cyano- or alkoxycarbonyl and n=1. According to these patents such compounds are prepared by reacting 3,4-dihydroisoquinoline with quaternary salts or unsaturated ketones. The compounds of this type have $R^1$ and $R^2$ as methoxy.

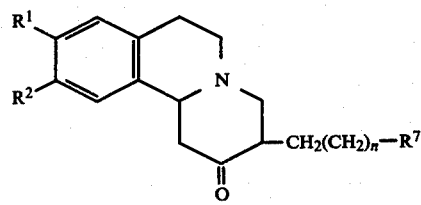

According to the process of the present invention the compounds can be made by reacting a compound of the formula (IV)

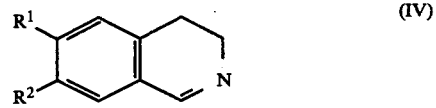

($R^1$ and $R^2$ are each ethyleneoxy or together are methylenedioxy) with a compound of the formula (V)

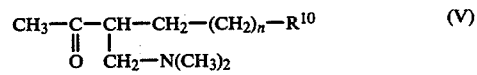

(wherein $R^{10}$ is a cyano- or alkoxycarbonyl with $C_1$ to $C_7$ alkoxy). In the compound thus obtained the $R^{10}$ group can be converted into an $R^7$ group by hydrolysis, ammonolysis, halogenating and/or esterification. The compound of the formula (II) or (III) can be converted into a pharmaceutically effective salt thereof.

The compounds of the formulas (II) or (III) may be transformed into salts of an inorganic acid (e.g. hydrochloric acid, hydrobromic acid, etc.) or organic acids (e.g. acetic acid, citric acid, etc.). Salt formation may also be carried out by methods known per se. One may proceed preferably by reacting a compound of the formula (I) with the solution of the corresponding acid formed with alcohol.

According to a further aspect of the present invention, there are provided a method of treatment and pharmaceutical compositions having antiinflammatory effect comprising as active ingredient a compound of the formula (II) or (III).

The pharmaceutical compositions of the present invention may be prepared by methods of pharmaceutical industry known per se. The compositions may be put up in solid (e.g. tablets, pills, coated pills, etc.) and liquid (e.g. solution, emulsion and suspension) form. The composition may be suitable for oral, parenteral and rectal administration. The inert diluents may be starch, calcium carbonate, magnesium stearate, magnesium carbonate, water, polyalkyleneglycol, etc.

The dosage of the active ingredient may vary within a wide range and depends on the requirements of the given case. Generally it may be stated that the daily dosage of the active ingredient formula (II) or (III) may be from about 300 mg to about 500 mg. It is preferred to use the compositions in a dosage unit formed by tablets or capsules comprising from about 50 mg to about 150 mg of a compound of the formula (II) or (III).

The benzo(a)quinolizidine derivatives of the formulas (II) and (III) possess valuable pharmacological effects, and can be used primarily as potent antiphlogistic agents for animal subjects. In the following there are summarized the pharmacological tests performed with the compounds of the formulas (II) and (III), and the results of these tests. The compounds examined in the pharmacological tests were represented by the following symbols:

| Symbol | $R^1$ | $R^2$ | $R^7$ | n |
|---|---|---|---|---|
| SC 118 | —O—CH$_2$—O— | | CN | 1 |
| SCT-1 | —OCH$_3$ | —OCH$_3$ | CN | 1 |
| SCT-2 | —OCH$_3$ | —OCH$_3$ | CH$_3$COO— | 1 |

-continued

| Symbol | R¹ | R² | R⁷ | n |
|---|---|---|---|---|
| SCT-3 | —OC$_2$H$_5$ | —OC$_2$H$_5$ | CN | 1 |

As evidenced by the results of the different tests, the benzo(a)quinolizidine derivatives of the formulas (II) and (III) possess the same or even more potent antiphlogistic effect than phenylbutazone.

Inhibition of kaolin- and carrageenin-induced oedema

The tests were carried out on groups each consisting of at least ten animals. The percentage inhibition of oedema, in relation to the untreated controls, was determined for each of the animals, and the average values were calculated. These average values are listed in Table 1 below.

TABLE 1

| Compound | Dosage mg/kg p.o. | Inhibition of Kaolin-Induced Oedema 2 Hours After Administration, % | Inhibiton of Carrageenin-Induced Oedema 1.5 Hours After Administration, % |
|---|---|---|---|
| SC 118 | 25 | 18.1+ | 22.0+ |
|  | 50 | 27.5+ | 30.6++ |
|  | 75 | 43.7++ | 47.7++ |
|  | 100 | 53.4++ | 52.7++ |
| SCT-1 | 25 | 20.5+ | — |
|  | 50 | 21.4+ | 24.2+ |
|  | 75 | 24.8+ | 25.7+ |
|  | 100 | 47.8++ | 37.7++ |
| SCT-2 | 25 | 5.8 | — |
|  | 50 | 21.4+ | 14.3 |
|  | 75 | 24.7+ | 2.8 |
|  | 100 | — | 17.0 |
| SCT-3 | 25 | 17.3+ | 25.1+ |
|  | 50 | 19.4+ | 41.5++ |
|  | 75 | 48.9++ | — |
|  | 100 | 45.9++ | 53.7++ |
| Phenylbutazone | 50 | 27.5++ | 24.3+ |
| Indomethacin | 10 | 27.2++ | 26.7+ |
| Na-salicylate | 100 | 10.5 | 16.2 |

+P = 0.01
++P = 0.05 (significance levels according to Student's "t" test)

Cotton granuloma test

TABLE 2

| COMPOUND | DOSAGE (mg/kg) | EFFECT, % | p |
|---|---|---|---|
| SC 118 | 50 | 26.4 | 0.01 |
| Phenylbutazone | 50 | 19.6 | 0.05 |
| Na-salicylate | 100 | 25.5 | 0.05 |

The benzo(a)quinolizidine derivatives according to the invention exert outstandingly high activities in the inhibition of serotonine-induced oedema, superseding many times the activities of phenylbutazone and indomethacin.

Tests performed on serotonine-induced oedema

The tests were carried out on groups each consisting of ten animals. The percentage inhibition of oedema, in relation to the untreated controls, was determined for each of the animals. The data listed in Table 3 are the averages of the inhibition values.

TABLE 3

| COMPOUND | DOSAGE (mg/kg) p.o. | PERCENTAGE INHIBITION 1 HOUR AFTER ADMINISTRA. |
|---|---|---|
| SC 118 | 25 | 28.5+ |
|  | 50 | 42.1+ |
|  | 75 | 48.7+ |
| SCT-1 | 50 | 22.4+ |
|  | 100 | 57.8+ |
| SCT-2 | 100 | 16.0 |
| SCT-3 | 50 | 36.2+ |
|  | 100 | 47.0+ |
| Phenylbutazone | 100 | 10.2 |
| Indomethacin | 25 | 1.4 |

+p = 0.001 (Student's "t" test)

Besides their antiphlogistic activities, some of the benzo(a)quinolizidine derivatives have antipyretic effects as well. On the basis of the tests performed on experimentally provoked fever, the antipyretic activities of the compounds according to the invention surpass the effect of amidazophenum.

Antipyretic activity

TABLE 4

| Compound | Dosage (mg/kg) p.o. | Variation of Body Temperature Hours After Administration | | |
|---|---|---|---|---|
| | | 1 | 2 | 3 |
| SC 118 | 50 | −2.75+++ | −3.34+++ | −4.03+++ |
|  | 25 | −1.67+++ | −1.81+++ | −1.60++ |
| Phenylbutazone | 50 | −1.05++ | −1.07++ | −0.76+ |
|  | 25 | −0.82++ | −0.84++ | −0.73+ |
| Amidazophenum | 25 | −1.17+++ | −0.94++ | −0.95++ |

+p = 0.05
++p = 0.01
+++p = 0.001

Furthermore, as evidenced by the results of the hotplate and writhing tests, the compounds according to the invention possess analgesic effects as well. In this respect the compounds according to the invention are superior to phenylbutazone.

Examination of the analgesic effect by the hotplate test

TABLE 5

| COMPOUND | DOSAGE (mg/kg) p.o. | PROLONGATION OF THE REACTION TIME, % (2 HOURS AFTER ADMINISTRATION) |
|---|---|---|
| SC 118 | 50 | 61.2 |
| SCT-2 | 50 | 26.4 |
| SCT-3 | 50 | 33.9 |
| Indomethacin | 50 | no evaluable effect |
| Phenylbutazone | 50 | can be observed |

Examination of the analgesic effect by the writhing test

TABLE 6

| COMPOUND | DOSAGE (mg/kg) p.o. | ACTIVITY, % (REDUCTION OF THE NUMBER OF WRITHINGS IN RELATION TO THE CONTROLS) |
|---|---|---|
| SC 118 | 50 | 41.8 |
| Phenylbutazone | 100 | 17.6 |

Besides the antiphlogistic and antipyretic effects, the new benzo(a)quinolizidine derivatives also have a sedative effect on the central nervous system.

Narcosis-potentiating effect

TABLE 7

| COMPOUND | DOSAGE (mg/kg) p.o. | PROLONGATION OF THE SLEEP PERIOD IN RELATION TO THE UNTREATED CONTROLS, % |
|---|---|---|
| SC 118 | 50 | 253.0 |
|  | 25 | 96.4 |
| SCT-1 | 50 | 207.6 |
|  | 25 | 132.8 |
| SCT-2 | 50 | 28.3 |
| SCT-3 | 50 | 240.2 |
|  | 25 | 131.7 |
| Meprobamate | 20 | 110.2 |

The results of the toxicity examinations indicate that most of the benzo(a)quinolizidine compounds according to the invention have about the same degree of toxicity as phenylbutazone.

Acute toxicity tests

The acute toxicity values of the compounds were determined on rats, after oral administration. The $LD_{50}$ values were calculated according to the Litchfield-Wilcoxon method. The results are summarized in Table 8.

TABLE 8

| COMPOUND | $LD_{50}$ mg/kg p.o. |
|---|---|
| SC 118 | 1407.63 |
| SCT-1 | 620 |
| SCT-3 | 780 |
| Aspirin | 1700 |
| Phenylbutazone | 1181.45 |
| Indomethacin | 12 |

In order to give a more detailed information, in the following there are given the results of the toxicity tests performed with compound SC 118. The tests were carried out on CFY rats, each weighing 150 to 200 g.

TABLE 9

| DOSAGE mg/kg | DEAD ANIMALS/TREATED ANIMALS 48 HOURS AFTER ADMINISTRATION | | | | | |
|---|---|---|---|---|---|---|
|  | m | f | m | f | m | f |
| 750 | 0/10 | 0/10 | 0/10 | 0/10 | 0/10 | 0/10 |
| 1000 | 1/10 | 2/10 | 2/10 | 2/10 | 2/10 | 2/10 |
| 1250 | 2/10 | 3/10 | 3/10 | 3/10 | 3/10 | 3/10 |
| 1500 | 5/10 | 6/10 | 5/10 | 6/10 | 5/10 | 6/10 |
| 1750 | 6/10 | 6/10 | 8/10 | 8/10 | 8/10 | 8/10 |
| 2000 | 10/10 | 10/10 | 10/10 | 10/10 | 10/10 | 10/10 |

$LD_{50}$, m = 1425 mg/kg
$LD_{50}$, f = 1400 mg/kg
m = male
f = female

When examining the subtoxic effects it appeared that none of the compounds according to the invention exert ulcerogeneous effects or harmful influence on the haematopoietic system, either. As a comparison it should be noted e.g. indomethacine has a marked ulcerogeneous effect.

Determination of ulcer index

Table 10

| Compound | Ulcer | | Erosion | |
|---|---|---|---|---|
|  | male | female | male | female |
| SC 118 | 0/10 | 0/10 | 0/10 | 0/10 |
| SCT-1 | 1/10 | 2/10 | 3/10 | 4/10 |
| SCT-3 | 1/10 | 0/10 | 6/10 | 4/10 |
| Control | 0/10 | 0/10 | 0/10 | 0/10 |
| Indomethacin | 3/10 | 3/10 | 1/10 | 1/10 |

Table 10-continued

| Compound | Ulcer | | Erosion | |
|---|---|---|---|---|
|  | male | female | male | female |
| Phenylbutazone | 3/10 | 1/10 | 0/10 | 0/10 |
| Na-salicylate | 4/10 | 2/10 | 1/10 | 3/10 |

Thus the benzo(a)quinolizidine derivatives of the formula (I) are substances with significant antiphlogistic effects, possessing valuable antipyretic and analgesic activities as well. The sedative effects of these compounds are also not negligible. Moreover, these compounds are completely devoid of the undesired side effects (e.g. ulcerogeneous effect) characteristic of the nonsteroidal antiphlogistic agents, and their therapeutical indices are far more favorable than that of indomethacin.

Therapeutical indices

Table 11

| Compound | Therapeutical Index $LD_{50}/ED_{50}$ | |
|---|---|---|
|  | kaolin-oedema | carrageenin-oedema |
| SC 118 | 29.2 | 22.6 |
| SCT-1 | 12.4 | 6.7 |
| SCT-3 | 15.0 | 19.8 |
| Indomethacin | 2.3 | 1.3 |

Based on the above, the compound according to the invention can be used as antiphlogistic and analgesic agents primarily in the treatment of disorders evoked by the inflammation of joints and skeletal musculature.

Because of their non-ulcerogeneous character and of the lack of harmful side effects on the haematopoietic system, these compounds can also be administered for a prolonged period, which is very desirable in the treatment of the above-mentioned disorders.

SPECIFIC EXAMPLES

Example 1

2-Oxo-3-(β-cyanoethyl)-9,10-methylenedioxy-1,2,3,4,6,7-hexahydro-11bH-benzo(a)quinolizidine 1.0 g. (5.92 mmoles) of 4-dimethylaminomethyl-5-oxo-capronitrile are added to a solution of 1.0 g. (4.95 mmoles) of 9,10-methylenedioxy-isoquinoline hydrochloride in 3 ml. of distilled water, and the mixture is allowed to stand for one day. The separated crystalline substance is filtered off, and washed successively with water and methanol. 0.9 g. (64%) of 2-oxo-3-(β-cyanoethyl)-9,10-methylenedioxy-1,2,3,4,6,7-hexahydro-11bH-benzo(a)quinolizidine are obtained; m.p.: 154°–155° C. (after recrystallization from methanol).

Characteristic IR-bands (in KBr): 2380 cm$^{-1}$ (CN), 1715 cm$^{-1}$ (C=O), 2750, 2800 cm$^{-1}$ (Bohlmann-bands).

NMR-spectrum (in deuterochloroform): τ=3.48 ($C_{11}$-H), 3.53 ($C_8$-H) and 4.18 (—O—CH$_2$—O—).

Example 2

2-Oxo-3-(β-cyanoethyl)-9,10-diethoxy-1,2,3,4,6,7-hexahydro-11bH-benzo(a)quinolizidine 1.0 g. (3.95 mmoles) of 9,10-diethoxyquinoline hydrochloride is dissolved in 3 ml. of distilled water, and 0.8 g. (4.75 mmoles) of 4-dimethylaminomethyl-5-oxo-capronitrile are added to the solution. The reaction mixture is allowed to stand for one day, thereafter the separated crystals are filtered off and washed successively with water and methanol. 1.2 g. (89%) of 2-oxo-3-(β-cyanoethyl)-9,10-diethoxy-1,2,3,4,6,7-hexahydro-11bH-benzo(a)quinolizidine are obtained; m.p.: 135°–136° C. (after recrystallization from methanol).

Characteristic IR-bands (in KBr): 2750, 2800 cm$^{-1}$ (Bohlmann-bands), 2300 cm$^{-1}$ (CN), 1710 cm$^{-1}$ (CO).

We claim:

1. An antiphlogistic method of treatment which comprises administering to a mammalian subject requiring such treatment a pharmaceutically effective dosage of a compound selected from the group which consists of:

2-oxo-3-(β-cyanoethyl)-9,10-methylenedioxy-1,2,3,4,6,7-hexahydro-11bH-benzo(a)quinilozidine,
2-oxo-3-(β-cyanoethyl)-9,10-diethoxy-1,2,3,4,6,7-hexahydro-11bH-benzo(a)quinilozidine,
and a pharmaceutically effective salt thereof.

2. The method defined in claim 1 wherein said compound is 2-oxo-3-(β-cyanoethyl)-9,10-methylenedioxy-1,2,3,4,6,7-hexahydro-11bH-benzo(a)quinilozidine or a pharmaceutically effective salt thereof.

3. The method defined in claim 1 wherein said compound is 2-oxo-3-(β-cyanoethyl)-9,10-diethoxy-1,2,3,4,6,7-hexahydro-11bH-benzo(a)quinilozidine or a pharmaceutically effective salt thereof.

* * * * *